US007138149B2

(12) United States Patent  
Cho

(10) Patent No.: US 7,138,149 B2
(45) Date of Patent: Nov. 21, 2006

(54) DIETARY SUPPLEMENTS AND METHODS FOR TREATING PAIN AND INFLAMMATION

(75) Inventor: Suk H. Cho, Idaho Falls, ID (US)

(73) Assignee: Melaleuca, Inc., Idaho Falls, ID (US)

(*) Notice: Subject to any disclaimer, the term of this patent is extended or adjusted under 35 U.S.C. 154(b) by 220 days.

(21) Appl. No.: 10/765,654

(22) Filed: Jan. 27, 2004

(65) Prior Publication Data

US 2004/0185035 A1 Sep. 23, 2004

Related U.S. Application Data

(62) Division of application No. 10/039,246, filed on Jan. 4, 2002, now Pat. No. 6,713,096.

(51) Int. Cl.
*A01N 65/00* (2006.01)
*A01N 55/08* (2006.01)
*A01N 31/69* (2006.01)
*A61K 38/43* (2006.01)
*A61K 9/20* (2006.01)

(52) U.S. Cl. ............... 424/756; 424/729; 424/94.1; 424/464; 514/62

(58) Field of Classification Search ........... 424/756, 424/729, 94.1, 464; 514/62
See application file for complete search history.

(56) References Cited

U.S. PATENT DOCUMENTS

| | | |
|---|---|---|
| 3,615,721 A | 10/1971 | Silberman |
| 3,758,682 A | 9/1973 | Huber et al. |
| 4,393,085 A | 7/1983 | Spradlin et al. |
| 4,698,360 A | 10/1987 | Masquelier |
| 4,737,364 A | 4/1988 | Kalogris |
| 5,009,891 A | 4/1991 | Niwa et al. |
| 5,308,627 A | 5/1994 | Umbdenstock, Jr. |
| 5,387,422 A | 2/1995 | Handel et al. |
| 5,565,435 A | 10/1996 | Yoneyama et al. |
| 5,567,424 A | 10/1996 | Hastings |
| 5,569,458 A | 10/1996 | Greenberg |
| 5,589,182 A | 12/1996 | Tashiro et al. |
| 5,626,849 A | 5/1997 | Hastings et al. |
| 5,904,924 A | 5/1999 | Gaynor et al. |
| 5,948,443 A | 9/1999 | Riley et al. |
| 5,976,568 A | 11/1999 | Riley |
| 6,030,621 A | 2/2000 | De Long et al. |
| 6,054,128 A | 4/2000 | Wakat |
| 6,210,679 B1 | 4/2001 | Bailey et al. |
| 6,344,220 B1 | 2/2002 | Rose et al. |
| 6,358,526 B1 * | 3/2002 | Mergens et al. |

OTHER PUBLICATIONS

Sharma, Jagdish N. et al. Pharmacology (Basel), (1994) vol. 49, No. 5, pp. 314-318. Suppressive effects of eugenol and ginger oil on arthritic rats. Abstract.*
Sharma, Jagdish N. et al. Pharmacology (Basel), (1994) vol. 49, No!. 5, pp. 314-318. Suppressive effects of eugenol and ginger oil on arthritic rats.*
PTOL-413B (Apr. 2003): Examiner-Initated Interview Summary dated Apr. 17, 2006 with attached "Dr. Stan Guberman Invoice".*
http://www.indena.it/pharmac.htm—Indena, Pharmaceuticals, printed from website Aug. 13, 2002.
http://www.thehealthstore.net/en-us/p_2.html. (Mar. 24, 2003). "Ultimate Joint Repair Formula".
http://www.rxvitamins.com/pets/nutriflex.asp. (Mar. 24, 2003), "Professional Veterinary Formulas: NutriFlex for Dogs and Cats".
http://www.unikeyhealth.com/products_cleansing_inflazyme.asp: American Biologics, (Rev. Jan. 2), Inflazyme Forte, Trademark.
http://www.vitaminexpress.com/prodinfo/wobenzym_n.htm. (Mar. 27, 2003), Vitamin Express, MaryIn Nutraceuticals, Inc. Wobenzym-N.
http://www.healingedge.net/store/more_mar_wobenzyme.htm. (Mar. 27, 2003), Wobenzyme N (Enzyme) 800 TB.
Balch and Balch, *Prescription for Nutritional Healing*, Second Edition, 1997, pp. 20-21 and 47-48.
Bombardelli, "Phytosome® : new cosmetic delivery system," *Boll. Chim. Farmaceutico*, 1991, 8 pgs.
Cao et al., "Increases in human plasma antioxidant capacity after consumption of controlled diets high in fruit and vegetables," *Am. J. Clin. Nutr.*, 1998, 68:1081-1087.
Dallas et al., "Degradation of oligomeric procyanidins and anthocyanins in Tinta Roriz red wine during maturation," *Vitis*, 1995, 34(1):51-56.
Demrow et al., "Administration of Wine and Grape Juice Inhibits In Vivo Platelet Activity and Thrombosis in Stenosed Canine Coronary Arteries," *Circulation*, 1995, 91:1182-1188.
Eichhorn et al., "Spontaneous Alterations in Coronary Blood Flow Velocity Before and After Coronary Angioplasty in Patients With Severe Angina," *JACC*, 1991, 17(1):43-52.

(Continued)

Primary Examiner—Michele Flood
(74) Attorney, Agent, or Firm—Fish & Richardson, P.C.

(57) ABSTRACT

The invention provides compositions such as dietary supplements. Such compositions can be used to reduce pain, inflammation, stiffness, and/or discomfort associated with inflammatory conditions such as arthritis. The invention also provides methods for reducing pain, inflammation, stiffness, and/or discomfort associated with inflammatory conditions such as arthritis.

13 Claims, No Drawings

OTHER PUBLICATIONS

Folts et al., "Platelet Aggregration in Partially Obstructed Vessels and its Elimination with Aspirin," *Circulation*, 1976, 54:365-370.

Folts et al., "Possible Platelet Thrombi Formation in Dog and Human Femoral Arteries," *Texas Heart Institute Journal*, 1982, 9(1):19-26.

Folts, "An In Vivo Model of Experimental Arterial Stenosis, Intimal Damage, and Periodic Thrombosis," *Circulation*, 1991, 83(Suppl. IV):IV-3—IV-14.

Folts et al., "Moderate alcohol consumption, CAD, and myocardial ischemia," *J. Myocardial Ischemia*, 1994, 6(8):33-40.

Folts, "Drugs for the Prevention of Coronary Thrombosis: From an Animal Model to Clinical Trials," *Cardiovasc. Drugs Ther.*, 1995, 9:31-43.

Folts, "Gastric Administration of a Commercial Flavonoid Dietary Supplement Inhibits In Vivo Platelet Activity and Cyclic Flow Reductions in Stenosed Monkey Carotid Arteries," *Supplement to Circulation*, Abstracts from the 68th Scientific Sessions, Anaheim, California, p. I-489, Abstract No. 2336.

Folts, "Flavonoid in Tea but not Coffee Given by Gastric Tube Inhibits In Vivo Platelet Activity and Thrombus Formation in Stenosed Dog Coronary Arteries," *FASEB J.*, 1996, p. A793, Abstract No. 4579.

Folts et al., "Grape Juice But Not Orange or Grapefruit Juice Significantly Inhibits In Vivo.Platelet Activity and Thrombosis in Stenosed Canine Coronary Arteries," *Supplement to JACC*, 1997, 29(2, Suppl. A):180A, Abstract No. 734-5.

Folts, "Three Glasses of Grape But Not Orange or Grapefruit Juice Inhibit Ex Vivo Platelet Aggregation in Human Volunteers," *Supplement to JACC*, 1997, 29(2, Suppl. A):226A, Abstract No. 767-3.

Folts and Osman, "Platelet Inhibitory Effect of Feeding Grape Juice But Not Orange or Grapefruit Juice for Seven Days in Monkeys," *Supplement to JACC*, 1997, 29(2, Suppl. A):303A, Abstract No. 1006-156.

Formica and Regelson, "Review of the Biology of Quercetin and Related Bioflavonoids," *Food Chem. Toxic.*, 1995, 33(12):1061-1080.

Haqqi et al., "Prevention of collagen-induced arthritis in mice by a polyphenolic fraction from green tea," *Proc. Natl. Acad. Sci. USA*, 1999, 96:4524-4529.

Hashimoto et al., "Effect of Acute Intake of Red Wine on Flow-Mediated Vasodilatation of the Brachial Artery," *Am. J. Cardiol.*, 2001, 88:1457-1460.

Morris et al., "Effects of Fruit Maturity, Juice Storage, and Juice Extraction Temperature on Quality of 'Concord' Grape Juice," *J. Amer. Soc. Hort. Sci.*, 1986, 111(5):742-746.

Preuss et al., "Effects of Niacin-Bound Chromium and Grape Seed Proanthocyanidin Extract on the Lipid Profile of Hypercholesterolemic Subjects: A Pilot Study," *J. Med.*, 2000, 31(5 & 6):227-246.

Singleton and Rossi, Jr., "Colorimetry of Total Phenolics with Phosphomolybdic-Phosphotungstic Acid Reagents," *Am. J. Enol. Vitic*, 1965, 16:144-158.

Slane et al., "Platelet Inhibition in Stenosed Canine Arteries by Quercetin and Rutin, Polyphenolic Flavonoids Found in Red Wine," *Clinical Research*, 1994, 42(2):162A, Abstract.

Strong, "Atherosclerosis in the Young: Risk and Prevention," *Hospital Practice*, 1999, pp. 15, 16 and 19.

Strong et al., "Prevalence and Extent of Atherosclerosis in Adolescents and Young Adults," *JAMA*, 1999, 281(8):727-735.

Waterhouse et al., "The Phenolic Phytochemicals in Wine, Fruit and Tea: Dietary Levels, Absorption and Potential Nutritional Effects," *Hypernutritious Foods*, 1997, Finley et al. (eds.), Agscience, Inc., Chapter 14, pp. 219-238.

Wood et al., "Sequential effects of an oral enzyme combination with rutosid in different in vitro and in vivo models of inflammation," *J. Immunotherapy*, 1997, 3/4:139-145.

* cited by examiner

DIETARY SUPPLEMENTS AND METHODS FOR TREATING PAIN AND INFLAMMATION

CROSS-REFERENCE TO RELATED APPLICATION

This application is a divisional (and claims the benefit of priority under 35 USC 120) of U.S. application Ser. No. 10/039,246, filed Jan. 4, 2002 now U.S. Pat. No. 6,713,096. The disclosure of the prior application is considered part of (and is incorporated by reference in) the disclosure of this application.

BACKGROUND

1. Technical Field

The invention relates to dietary supplements as well as methods for reducing pain, inflammation, and stiffness associated with inflammatory conditions such as arthritis.

2. Background Information

Inflammatory conditions such as arthritis and osteoarthritis are serious medical problems that affect many Americans. In fact, arthritis is one of the nation's most prevalent chronic health problems. An estimated 43 million Americans suffer from some form of arthritis. According to the Arthritis Foundation, this figure is expected to jump to about 60 million within the next decade.

Osteoarthritis (OA), also known as degenerative joint disease, is the most common form of arthritis. By age 40, about 90 percent of all people have x-ray evidence of OA in the weight bearing joints such as the hips and knees. In addition, more than 20 million American currently have symptoms of OA. Severe involvement of the hips, knees, and spinal column can greatly limit activity and diminish the overall quality of life. The gradual breakdown of cartilage that accompanies aging is the leading cause of OA. This type of OA, called primary osteoarthritis, is caused by cartilage damage resulting mostly from stress on the joint from, for example, obesity. The first alteration in the joint, which takes place over decades, is a roughening of articular cartilage followed by pitting, ulceration, and progressive loss of cartilage surface. Primary OA most commonly involves the joints of the fingers, hips, knees, spine, base of the thumb, and big toe. It can be present in just one of these joints or in all of them.

Secondary OA, however, can affect any joint. Typically, secondary OA follows trauma or chronic joint injury due to some other type of arthritis such as rheumatoid arthritis. Alternatively, secondary OA can result from overuse of a particular joint. Although most body tissues can make repairs following an injury, cartilage repair is hampered by a limited blood supply and the lack of an effective mechanism for cartilage re-growth. The effects of joint overuse were shown in a study that revealed that subjects whose jobs required at least one hour a day of kneeling or squatting were almost twice as likely to have OA in the knees than those not commonly performing such activities. Because trauma or overuse hastens the degeneration of cartilage, symptoms of secondary OA can become apparent at a much younger age than symptoms of primary OA.

OA symptoms are usually mild at first. For example, morning stiffness that rarely lasts for more than 15 minutes is a common early symptom of OA. As the disease advances, mild pain will occur when moving the affected joint. The pain typically is made worse by greater activity and is relieved by rest. In many people, symptoms progress no further. In others, however, the pain and stiffness gradually worsen until they limit daily activities such as walking, going up stairs, or typing. Enlargement of the finger joints is common in the later stages of OA. Knobby overgrowths of the joints nearest the fingertips occur most often in women and tend to run in families.

There are number of treatments that can relive the pain, inflammation, and discomfort associated with OA. One treatment involves the use of non-steroidal anti-inflammatory drugs (NSAIDs). Although NSAIDs relieve some stiffness, inflammation, and pain associated with OA, NASIDs can lead to side effects such as gastric bleeding, liver damage, and kidney damage. In addition, long-term use of NSAIDs can lead to reduced effectiveness.

SUMMARY

The invention provides compositions (e.g., dietary supplements) for reducing pain, inflammation, and/or stiffness associated with inflammatory conditions such as arthritis or OA. Reducing pain, inflammation, or stiffness associated with an inflammatory condition can help improve joint mobility. Typically, such compositions can contain an aminosaccharide, a ginger component, and an enzyme. In addition, the compositions provided herein can contain other ingredients such as a green tea extract. The compositions provided herein can be used to help people live healthier, more active lives by reducing joint pain, inflammation, or stiffness and/or by rebuilding cartilage. The compositions of the invention also provide people suffering from joint problems with a treatment that can produce detectable benefits within a short time period (e.g., within a few days of the first administration). In addition, the compositions of the invention can provide people suffering from joint problems with a safe treatment containing natural ingredients. The invention also provides methods for reducing pain, inflammation, and/or stiffness associated with inflammatory conditions such as arthritis.

In one aspect, the invention provides a dietary supplement comprising an aminosaccharide, a ginger component, and an enzyme. An aminosaccharide can be an aminosaccharide salt. Representative aminosaccharides include glucosamine, glucosamine hydrochloride, glucosamine sulfate, glucosamine phosphate, glucosamine lactate, or glucosamine dodecanoate. Typically, 300 mg to 3000 mg (e.g., 1000 mg to 2000 mg) of the dietary supplement is the aminosaccharide. A ginger component can include ginger oil, gingerroot or gingerroot extract. Typically, 50 mg to 10 g (e.g., 100 mg to 500 mg) of the dietary supplement is the ginger component.

Representative enzymes that can be included in a dietary supplement of the invention are bromelain, papain, fungal proteases, acid stable proteases, neutral stable proteases, and alkaline stable proteases. A dietary supplement of the invention can include a single enzyme or at least two different enzymes. Typically, 50 mg to 10 g (e.g., 1000 mg to 2000 mg) of the dietary supplement is the enzyme. A dietary supplement of the invention can be in the form of a tablet, a powder, or a liquid. A dietary supplement can include a green tea extract. Typically, 50 mg to 2000 mg (e.g., 100 mg to 1000 mg) of the dietary supplement is the green tea extract.

A dietary supplement of the invention can reduce pain, stiffness, or inflammation in a mammal. Generally, administration of the dietary supplement to a mammal reduces pain, stiffness, or inflammation in the mammal within four hours of the administration. In addition, daily administration of the dietary supplement to a mammal for at least two weeks generally reduces pain, stiffness, or inflammation in the mammal.

In another aspect, the invention provides a dietary supplement comprising: (a) at least about 1500 mg of a glucosamine salt, (b) at least about 175 mg of a ginger extract, (c) at least about 125 mg of a green tea extract, and (d) at least about 50 mg of bromelain. In yet another aspect, the invention provides a tablet comprising: (a) at least about 500 mg of glucosamine hydrochloride, (b) at least about 60 mg of a ginger extract, (c) at least about 20 mg of a green tea extract, and (d) at least about 20 mg of bromelain.

In still another aspect, the invention provides a method for reducing pain, inflammation, stiffness, or discomfort in a mammal, the method comprising administering a dietary supplement, to the mammal, in an amount effective to reduce the pain, inflammation, stiffness, or discomfort, wherein the dietary supplement comprises an aminosaccharide, a ginger component, and an enzyme. A representative aminosaccharide is glucosamine. Generally, the mammal receives a daily dose of the glucosamine. A daily dose can be between 2 mg/Kg and 20 mg/Kg of body weight of the glucosamine. A representative ginger component is ginger oil. Generally, the mammal receives a daily dose of the ginger oil. A daily dose can be between 25 mg/Kg and 50 mg/Kg of body weight of the ginger oil.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides methods and materials related to reducing pain, inflammation, and/or stiffness associated with inflammatory conditions such as arthritis and OA. Specifically, the invention provides compositions (e.g., dietary supplements) containing an aminosaccharide, a ginger component, and an enzyme. In addition, the compositions provided herein can contain other ingredients such as a green tea extract.

Aminosaccharide

A composition of the invention can contain an aminosaccharide. Examples of aminosaccharides include, without limitation, aminomonosaccharides such as glucosamine, galactosamine, allosamine, mannosamime, and fructosamine. Aminomonosaccharides such as glucosamine can be found in glycoprotiens and/or glycoaminoglycans. Glucosamine can be obtained at high purity from hydrolyses of chitin obtained from shellfish or other crustacean. Glucosamine has following structure (I) and is typically in a salt form.

Structure (I):

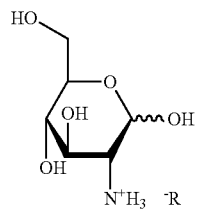

where R is an anion such as sulfate, chloride, phosphate, fluoride, bromide, or acetate. In addition, R can be a carboxylate from a carboxylic acid containing C3–C20. Further, R can be an amino acid that has a net charge of −1 such as glutamic acid or aspartic acid.

Other examples of aminosaccharides include, without limitation, short chain oligomers or polymers of aminosaccharides such as aminodisaccharides, aminotrisaccharides, aminotetrasaccharides, aminopentasaccharides, and aminooligosaccharides.

Aminosaccharides can be synthesized or derivitized from natural sources. In addition, aminosaccharides can be obtained commercially. For example, glucosamine can be obtained from Technical Sourcing International (Missoula, Mont.), DNP International Co., Inc. (Terre Haute, Ind.), Battlechem Distribution (Westminster, Calif.), Zeta Pharm (Long Beach, Calif.), or Stauber Performance Ingredients Inc. (Fullerton, Calif.).

A composition of the invention can contain one or more than one aminosaccharide. For example, a dietary supplement can contain glucosamine as well as galactosamine. In addition, a composition can contain any amount of an aminosaccharide. For example, at least 5 percent (e.g., at least 10, 15, 20, 25, 30, 35, 40, 50, 60, 70, 80, or 90 percent) of a dietary supplement can be aminosaccharide. Typically, a dietary supplement contains between 50 mg and 5000 mg of an aminosaccharide such as glucosamine. A composition can be formulated to contain an amount of aminosaccharide such that a daily dose of between 300 mg to 3000 mg aminosaccharide (e.g., between 1000 mg to 2000 mg aminosaccharide) can be conveniently administered.

Ginger

A composition of the invention can contain a ginger component. Examples of ginger components include, without limitation, dried ginger (e.g., dried gingerroot), ginger oil, and ginger extracts. A ginger component can be obtained from any of the estimated 1300 species of plants that belong to the Zingiberaccae family. Typically, a ginger component is derived from *Zingiber officinale, Alpinia officnarum*, or *Alpinia galanga*.

Any method can be used to prepare a ginger component. For example, standard harvesting and drying methods can be used to prepare dried gingerroot. Ginger oil can be obtained using standard methods and processed with cellulose for making tablet or powder compositions. A ginger extract can be made using an ethanol or hydroalcoholic extraction. Such extracts can be standardized to, for example, 5 to 75 percent gingerol or shogaol. In addition, ginger components can be obtained commercially. For example, dried ginger, ginger oil, and ginger extract can be obtained from Buckton Scott Nutrition, Inc. (Fairfield, N.J.), FCC Inc. (NJ), Pure World, Inc (Hackensack, N.J.), or Sabinsa Corporation (Piscataway, N.J.).

A composition of the invention can contain one or more than one ginger component. For example, a dietary supplement can contain dried gingerroot as well as ginger extract. In addition, a composition can contain any amount of a ginger component. For example, at least 5 percent (e.g., at least 10, 15, 20, 25, 30, 35, 40, 50, 60, 70, 80, or 90 percent) of a dietary supplement can be a ginger component. Typically, a dietary supplement contains between 5 mg and 50 g of a ginger component. A composition can be formulated to contain an amount of a ginger component such that a daily dose of between 50 mg to 1000 mg ginger component (e.g., between. 100 mg to 500 mg ginger component) can be conveniently administered. For example, a composition can be formulated to contain 100 mg of a ginger component. When dried gingerroot is used, the composition can be formulated to contain an amount of dried gingerroot such that a daily dose of between 150 mg to 10 g dried gingerroot (e.g., between 1000 mg to 5000 mg dried gingerroot) can be conveniently administered. When ginger oil is used, the composition can be formulated to contain an amount of ginger oil such that a daily dose of between 50 mg to 1000 mg ginger oil (e.g., between 100 mg to 500 mg ginger oil) can be conveniently administered. The ginger oil can be extracted with hydrocarbon solvent or distilled to provide 1 to 50 percent gingerol and shogaol. When ginger extract is used, the composition can be formulated to contain an amount of ginger extract such that a daily dose of between 100 mg to 2000 mg ginger extract (e.g., between 150 mg to 1000 mg ginger extract) can be conveniently administered.

Enzyme and Enzyme Mixtures

A composition of the invention can contain an enzyme. Examples of enzymes include, without limitation, bromelain, papain, fungal proteases, acid stable proteases, neutral stable proteases, and alkaline stable proteases. Enzymes useful in the invention can be derived from any source such as porcine, bovine, fungi, or plants.

Any method can be used to obtain an enzyme. For example, standard protein isolation techniques can be used to obtain an enzyme preparation. In addition, enzymes such as bromelain and papain can be obtained commercially. For example, enzymes can be obtained from National Enzyme Company (Forsyth, Mont.), American Laboratories. Incorporated (Omaha, Nebr.), Botanical International (Long Beach, Calif.), or Marcor Development Corporation (Carlstadt, N.J.).

A composition of the invention can contain one or more than one enzyme. For example, a dietary supplement can contain a single enzyme or an enzyme blend. In addition, a composition can contain any amount of enzyme. For example, at least 5 percent (e.g., at least 10, 15, 20, 25, 30, 35, 40, 50, 60, 70, 80, or 90 percent) of a dietary supplement can be enzyme. Typically, a dietary supplement contains between 5 mg and 50 g of an enzyme. A composition can be formulated to contain an amount of enzyme such that a daily dose of between 25 mg to 2000 mg enzyme (e.g., between 50 mg to 1000 mg enzyme) can be conveniently administered. For example, a composition can be formulated to contain 50 mg of an enzyme blend.

Green Tea Extract

A composition of the invention can contain a green tea extract. A green tea extract is an extract derived from *Camellia sinensis*. Any method can be used to obtain a green tea extract. For example, a green tea extract can be obtained by drying (e.g., freeze drying or spray drying) a liquor from an alcoholic, hydroalcoholic, or other hydrocarbon extraction. In addition, a green tea extract can be dried and standardized to contain at least about 25 percent total phenols. A green tea extract can contain catechin, epicatechin, gallocatechin, epigallocatechin, epicatechin gallate, and epicatchingallate. Typically, a composition provided herein contains a green tea extract having at least about 15 percent of catechin group compounds. A green tea extract can be caffeinated or decaffeinated. In addition, a green tea extract can be obtained commercially. For example, a green tea extract can be obtained from Buckton Scott Nutrition, Inc. (Fairfield, N.J.), Pure World, Inc. (Hackensack, N.J.), Sabinsa Corporation (Piscatawayt, N.J.), or Stauber Performance Ingredients Inc., (Fullerton, Calif.).

A composition of the invention can contain one or more than one green tea extract. In addition, a composition can contain any amount of a green tea extract. For example, at least 5 percent (e.g., at least 10, 15, 20, 25, 30, 35, 40, 50, 60, 70, 80, or 90 percent) of a dietary supplement can be a green tea extract. Typically, a dietary supplement contains between 10 mg and 20 g of a green tea extract. A composition can be formulated to contain an amount of a green tea extract such that a daily dose of between 50 mg to 2000 mg of a green tea extract (e.g., between 100 mg to 1000 mg of a green tea extract) can be conveniently administered. For example, a composition can be formulated to contain 50 mg of a green tea extract.

Radical Scavengers, Antioxidants, and Reducing Agents

A composition of the invention can contain one or more radical scavengers, antioxidants, reducing agents, or mixtures thereof. Typically, a dietary supplement contains one or more radical scavengers, antioxidants, reducing agents, or mixtures thereof in an amount that effectively reduces oxidation or degradation of the ginger component, enzyme component, and/or green tea extract component of the composition. Examples of radical scavengers and antioxidants include, without limitation, ascorbic acid, tocopheryl acetate, tocopheryl palmitate, tocopherol, and butyl hydroxytoluene. Sodium bisulfite is an example of a reducing agent that can be incorporated into a dietary supplement.

A composition can contain any amount of radical scavengers, antioxidants, reducing agents, or mixtures thereof. For example, at least 1 percent (e.g., at least 2, 3, 4, 5, 6, 7, 8, 9, 10, 15, or 20 percent) of a dietary supplement can be a radical scavenger, antioxidant, reducing agent, or mixture thereof. Typically, a dietary supplement contains between 5 mg and 100 g of a radical scavenger, antioxidant, reducing agent, or mixture thereof.

Botanical Extracts

A composition of the invention can contain one or more botanical extracts (e.g., herbal extracts). Examples of botanical extracts include, without limitation, extracts from chamomile, rosemary, aloe, nettle, centella asiatica, ginkgo biloba, bilberry, apple, citrus bioflavonoids, garlic powder, olive oil, and/or blueberry. Such extracts can be dispersible or soluble in aqueous medium.

Any method can be used to obtain a botanical extract. For example, a botanical extract can be obtained from an alcoholic, hydroalcoholic, or other hydrocarbon extraction. In addition, a botanical extract can be obtained commercially. For example, a botanical extract can be obtained from Botanicals International (Long Beach, Calif.).

A composition can contain any amount of a botanical extract. For example, at least 1 percent (e.g., at least 2, 3, 4, 5, 6, 7, 8, 9, 10, 15, or 20 percent) of a dietary supplement can be a botanical extract. Typically, a dietary supplement contains between 5 mg and 100 g of a botanical extract.

Other Elements

A composition of the invention can contain vitamins and/or minerals. Examples of vitamins and minerals include, without limitation, pyridoxine chloride, gluthione, calcium citrate, magnesium citrate, magnesium oxide, calcium carbonate (e.g., lead-free calcium carbonate), ascorbic acid, zinc acetate, and vitamin B complexes. Vitamins and minerals can help reduce inflammation and rebuild joint cartilage.

In addition, a composition of the invention can contain more than one vitamin. For example, a composition can contain two different vitamins. Likewise, a composition of the invention can contain more than one mineral. For example, a composition can contain two different minerals.

Any method can be used to obtain a vitamin or mineral. For example, vitamins and minerals can be obtained using standard techniques. In addition, vitamins and minerals can be obtained commercially.

A composition can contain any amount of vitamins and minerals. For example, at least 1 percent (e.g., at least 2, 3, 4, 5, 6, 7, 8, 9, 10, 15, or 20 percent) of a dietary supplement can be vitamins and/or minerals. Typically, a dietary supplement contains between 5 mg and 100 g of vitamins and/or minerals.

Formulations of a Dietary Supplement

The present invention provides compositions (e.g., dietary supplements) containing a combination of an aminosaccharide, a ginger component, and an enzyme as well as other ingredients such as a green tea extract. Such compositions can be used to relieve pain, inflammation, and uncomfortableness due to, for example, OA. In addition, the invention provides methods for relieving or reducing pain, inflammation, and/or uncomfortableness due to, for example, OA. Such methods involve the administration of a composition provided herein.

The compositions provided herein are intended to be ingested (e.g., orally or intragastrically), but can be administered to a mammal by other routes. For example, a composition provided herein can be administered nasally, intravenously, intramuscularly, subcutaneously, sublingually, intrathecally, or intradermally. The route of administration can depend on a variety of factors, such as the environment (e.g., the circumstances resulting in the condition or symptoms) and therapeutic goals.

When administered orally, the composition can be in the form of a tablet or powder. Tablets and powders can be configured to have a unit dosage equal to the daily desired dosage. For example, if a mammal desires 1000 mg of a particular composition, each tablet can be 1000 mg in weight. As used herein, mammals generally refer to humans, but also can include domesticated mammals (e.g., dogs, cats, and livestock such as cows, horses, pigs, or sheep) in which reducing pain, inflammation, and/or stiffness is desirable.

The dosages of a particular composition will depend on many factors including the mode of administration. A dietary supplement of the invention can be formulated in a dose such that an individual receives about 1500 mg of glucosamine salt, 50 to 1000 mg of a ginger extract, 50 to 2000 mg of a green tea extract, and at least 2 mg/Kg of body weight of enzyme blend in a single tablet.

By way of example, a composition of the invention can be in the form of a liquid, solution, suspension, tablet, powder, cream, mist, atomized vapor, aerosol, soft gelatin capsules, or hard gelatin capsules. Commercial dietary supplements are generally formulated for oral administration. For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. Liquid preparations also can contain pharmaceutically acceptable additives such as suspending agents, emulsifying agents, non-aqueous vehicles, preservatives, buffer salts, flavoring agents, coloring agents, and sweetening agents as appropriate. Preparations for oral administration can be suitably formulated to give controlled release of the compound. Typically, the compositions provided herein are in a powder or tablet form with a fast disintegration time.

In addition, a composition provided herein can contain a pharmaceutically acceptable carrier for in vivo administration to a mammal. Such pharmaceutically acceptable carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include water, alcohol, saline, and buffered solutions. Pharmaceutically acceptable carriers also can include physiologically acceptable aqueous vehicles (e.g., physiological saline) or other known carriers appropriate to specific routes of administration. Preservatives, flavorings, and other additives such as, for example, proteins, anti-microbials, chelating agents, inert gases, and the like also can be present in a composition.

The invention will be further described in the following examples, which do not limit the-scope of the invention described in the claims.

EXAMPLES

Example 1

Dietary Supplements and Tablet Production

Tablet formulation #1 was made using the following ingredients in the amounts indicated:

| Ingredient | Amount |
| --- | --- |
| Glucosamine HCl | 510.00 mg |
| Calcium Carbonate | 269.90 mg |
| Ginger Root Extract | 60.00 mg |
| Microcrystalline Cellulose | 56.00 mg |
| Bromelain | 25.00 mg |
| Green Tea Extract Powder | 20.00 mg |
| Stearic Acid | 20.00 mg |
| Hydroxy Propyl Cellulose | 17.60 mg |
| Croscarmellose Sodium | 15.00 mg |
| Silicon Dioxide | 6.00 mg |
| Magnesium Stearate | 0.50 mg |

Tablet formulation #2 was made using the following ingredients in the amounts indicated:

| Ingredient | Amount |
| --- | --- |
| Glucosamine HCl | 750.00 mg |
| Dicalcium phosphate | 269.90 mg |
| Ginger Root Extract | 180.00 mg |

-continued

| Ingredient | Amount |
| --- | --- |
| Microcrystalline Cellulose | 56.00 mg |
| Bromelain | 50.00 mg |
| Green Tea Extract Powder | 50.00 mg |
| Stearic Acid | 20.00 mg |
| Acacia powder | 17.60 mg |
| Sodium starch glycolate | 15.00 mg |
| Silicon Dioxide | 6.00 mg |
| Calcium Stearate | 0.50 mg |

Tablet formulation #3 was made using the following ingredients in the amounts indicated:

| Ingredient | Amount |
| --- | --- |
| Glucosamine Sulfate | 510.00 mg |
| Calcium Carbonate | 269.90 mg |
| Ginger Root Extract | 100.00 mg |
| Microcrystalline Cellulose | 56.00 mg |
| Bromelain | 75.00 mg |
| Green Tea Extract Powder | 75.00 mg |
| Stearic Acid | 20.00 mg |
| Hydroxy Propyl Cellulose | 17.60 mg |
| Croscarmellose Sodium | 15.00 mg |
| Silicon Dioxide | 6.00 mg |
| Calcium Stearate | 0.50 mg |

The following procedure was performed-to make a tablet formulation #1, tablet formulation #2, and tablet formulation #3.

Weighing

All materials to be weighed were moved to a weighing area. After weighing, each ingredient was placed into a clean, poly lined container that was appropriately labeled.

Granulation

The solvent (water) and binder (hydroxypropylcellulose) were placed into a clean, stainless steel liquid mixer until the binder was dissolved. Glucosamine was placed into a separate clean, dry, stainless steel mixer and dry mixed for four minutes. With the mixer running, the solvent/binder solution was slowly added. The mixing continued until a uniform agglomeration occurred. Additional solvent was added, if all the material did not become wet and agglomerated. Each resulting wet granulation was placed on a clean, lined tray to a thickness of about one inch. Each granulation was dried in a drying room for about six hours at 42° C. Each dried granulation was checked for moisture content using a moisture analyzer. The moisture content should be within 1 percent of the moisture content of the materials prior to granulating. If additional drying was required, the material was returned to the drying room. Each dried granulation was milled through a clean, dry, stainless steel mill (Model D Fitzmill). Each milled granulation was placed in clean, poly lined containers that were properly labeled.

Premix

Bromelain, calcium carbonate, ginger root extract, and silicon dioxide were placed into a clean, dry, stainless steel V-blender. Large quantity materials were added first and last with small quantity materials being added in the middle. The mixture was mixed for ten minutes. After blending, the mixture was checked for lumping and uniformity. If either lumping or non-uniformity was noted, the material was screened and remixed. If the blend was uniform, the premix mixture was placed into a clean, poly lined container that was properly labeled.

Blending

The premix mixture and the milled granulation mixture were placed into a clean, dry, stainless steel V-blender. Green tea extract powder, magnesium stearate, stearic acid, microcrystalline cellulose, and croscarmellose sodium were screened and then added. Large quantity materials were added first and last with small quantity materials being added in the middle. The mixture was mixed for ten minutes. After blending, the resulting mixture was screened and then blended for an additional two minutes if lumping or non-uniformity was observed. The resulting blended mixture was placed into a clean, poly lined container properly labeled for compressing.

Compressing

The resulting blended mixture was pressed into tablet using a clean tablet press (Manesty; Stoke Company). Once pressed to the specification, each tablet was discharged through a tablet deduster and collected in a clean, poly lined corrugated container.

Coating

The tablets were placed onto a clean, dry, side-vented, stainless steel coating pan. The coating system settings used in the Vector High Coater 170 were as follows:

Mist checkers set to read 100/Atomization air, and 120 pattern air, total air 220

Nozzle air set to 65 to 70 psi

Fluid gear pump set to 90 mL/minute delivery rate/gun

Spray guns positioned 9 to 10 inches from the rotating tablet bed

Heater intake set to 90° C.

Control airflow set to obtain 40° C. exhaust air temperature

Pan rotation speed set to 4 rpm for Model 150 pan and 2.5 rpm for Model 170 pan

The tablet bed was gently heated to 30 to 35° C. When a tablet bed temperature of 30 to 35° C. was reached, the coating pan was continuously rotated and the spray coating initiated. The coating continued to obtain a 1.5 percent weight gain over the weight of an un-coated tablet. Upon completion of spray coating, pan rotation continued and about 300 to 400 gm of fine powder Carnauba Wax 13-300 was applied. The pan rotation continued until a high gloss was obtained. The tablets were dried in the jogging pan with the air on for about ten 10 minutes to remove moisture. The tablets were then collected into a clean, lined, corrugated container.

Example 2

Dietary Supplements Formulated as a Powder

Powder formulation #1 was made using the following ingredients in the amounts indicated. These amounts can equal the amount needed in a daily serving.

| Ingredient | Amount |
| --- | --- |
| Glucosamine sulfate | 1525.00 mg |
| Calcium Citrate | 100.00 mg |
| Ginger Root Extract | 275.00 mg |
| Fructooligosaccharides | 1500.00 mg |

-continued

| Ingredient | Amount |
| --- | --- |
| Maltodextrin | 2500.00 mg |
| Bromelain | 125.00 mg |
| Green Tea Extract | 500.00 mg |
| Flavoring agent | 5.00 mg |
| Ascorbic Acid | 75.00 mg |
| Tartaric acid | 15.00 mg |
| Silicon Dioxide | 4.00 mg |
| Fructose | 1500.00 mg |

Example 3

Dietary Supplements Formulated as a Capsule

Capsule formulation #1 was made using the following ingredients in the amounts indicated:

| Ingredient | Amount |
| --- | --- |
| Glucosamine HCl | 510.00 mg |
| Calcium Citrate | 100.00 mg |
| Ginger Root Extract | 75.00 mg |
| Rice flour | 56.00 mg |
| Enzyme blend* | 70.00 mg |
| Green Tea Extract | 75.00 mg |
| Magnesium Stearate | 10.00 mg |
| Hydroxy Propyl Cellulose | 50.00 mg |
| Silicon Dioxide | 6.00 mg |

*Enzyme blend contains fungal protease, acid protease, and papain

Example 4

Reducing Pain, Inflammation, Stiffness, and Discomfort using Dietary Supplements Two humans suffering from joint problems started taking three tablets daily. The tablets were tablet formulation #1 tablets described in Example 1. The tablets were taken in the mid morning with or without breakfast. After a few days to a week, each person reported noticeable improvement. The improvements included a reduction in pain and stiffness in their joints.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing pain, inflammation, stiffness, or discomfort in a mammal, said method comprising administering a dietary supplement to said mammal in an amount effective to reduce said pain, inflammation, stiffness, or discomfort, wherein said dietary supplement comprises an aminosaccharide, a ginger component, and an enzyme, wherein said aminosacchoride is granulated glucosamine or a granulated glucosamine salt selected from the group consisting of glucosamine hydrochloride, glucosamine sulfate, glucosamine phosphate, glucosamine lactate, and glucosamine dodecanoate; wherein said dietary supplement is in the form of a tablet; and wherein about 40% to about 55% of said tablet by weight is said aminosaccharide.

2. The method of claim 1, wherein said mammal receives a daily dose of said glucosamine, said daily dose being between 2 mg/kg and 20 mg/kg of body weight of said glucosamine.

3. The method of claim 1, wherein said ginger component is ginger oil.

4. The method of claim 3, wherein said mammal receives a daily dose of said ginger oil, said daily dose being between 25 mg/kg and 50 mg/kg of body weight of said ginger oil.

5. The method of claim 1, wherein said ginger component is gingerroot or gingerroot extract.

6. The method of claim 1, wherein about 5% to about 15% of said tablet by weight is said ginger component.

7. The method of claim 1, wherein said enzyme is selected from the group consisting of bromelain, papain, frugal proteases, acid stable proteases, neutral stable proteases, and alkaline stable proteases.

8. The method of claim 1, wherein about 1% to about 10% of said tablet by weight is said enzyme.

9. The method of claim 1, wherein said dietary supplement comprises at least two different enzymes.

10. The method of claim 1, wherein said dietary supplement comprises a green tea extract.

11. The method of claim 10, wherein about 1% to about 10% of said tablet by weight is said green tea extract.

12. The method of claim 1, wherein daily administration of said dietary supplement to a mammal for at least two weeks reduces pain, stiffness, or inflammation in said mammal.

13. The method of claim 1, wherein said tablet ranges in weight from about 1000 mg to about 1500 mg.

* * * * *